USOO5753454A

United States Patent [19]
Lee

[11] Patent Number: 5,753,454
[45] Date of Patent: May 19, 1998

[54] SEQUENCING OF OLIGOSACCHARIDES: THE REAGENT ARRAY-ELECTROCHEMICAL DETECTION METHOD

[75] Inventor: Cheng S. Lee, Ames, Iowa

[73] Assignee: Iowa State University Research Foundation, Inc., Ames, Iowa

[21] Appl. No.: 527,032

[22] Filed: Sep. 12, 1995

[51] Int. Cl.[6] .................... C12Q 1/34; C12Q 1/54; C12Q 1/00
[52] U.S. Cl. .................... 435/18; 435/14; 435/4; 435/25; 435/817; 435/72; 205/81; 204/298.03
[58] Field of Search ............... 435/18, 14, 817, 435/4, 25, 72; 205/81; 204/298.03

[56] References Cited

U.S. PATENT DOCUMENTS

| | | | |
|---|---|---|---|
| 5,100,778 | 3/1992 | Rademacher et al. | 435/18 |
| 5,284,558 | 2/1994 | Linhardt et al. | 204/182.8 |

FOREIGN PATENT DOCUMENTS

| | | |
|---|---|---|
| 0 421972A2 | 10/1991 | European Pat. Off. . |
| WO 92/02816 | 2/1992 | WIPO . |
| WO 92/19768 | 11/1992 | WIPO . |
| WO 92/19974 | 11/1992 | WIPO . |

OTHER PUBLICATIONS

J.R. Barr et al., "Structural Classification of Carbohydrates in Glycoproteins by Mass Spectrometry and High-Performance Anion-Exchange Chromatography[1]," *Analytical Biochemistry*, 192, pp. 181-192, (1991). Month Not Available.

C.J. Edge et al., "Fast Sequencing of Oligosaccharides: The Reagent-Array Analysis Method," *Proc. Nat'l. Acad. Sci. USA*, 89, pp. 6338-6342, (1992). Month Not Available.

Mike Geisow, "Shifting Gear in Carbohydrate Analysis," *Bio/Technology*, 10, pp. 227-280, (1992). Month Not Available.

Glyko, Inc., "FACE© Electrophoresis Products; FACE© Technology Description:," 4 pages. Month Not Available.

Peter Jackson, "The use of polyacrylamide-gel electrophoresis for the high-resolution separation of reducing saccharides labelled with the fluorophore 8-aminonophthalene-1,3,6-trisulphonic acid," *Biochem. J.*, 270, pp. 705-713, (1990). Month Not Available.

D.C. Johnson et al., "Liquid Chromatography with Pulsed Electrochemical Detection at Gold and Platinum Electrodes," *Analytical Chemistry*, 62, pp. 589A-597A, (1990). Month Not Available.

Akira Kobata, in *Biology of Carbohydrates*, vol. 2, V. Ginsburg et al., ed., John Wiley & Sons, New York, pp. 87-161, (1984). Month Not Available.

Akira Kobata, "Use of Endo- and Exoglycosidases for Structural Studies of Glycoconjugates[1]." *Anal. Biochem.*, 100, pp. 1-14, (1979). Month Not Available.

James C. Paulson, "Glycoproteins: what are the sugar chains for?," *Trends Biochem. Sci.*, 14, pp. 272-276, (1989). Month Not Available.

Michael W. Spellman, "Carbohydrate Characterization of Recombinant Glycoproteins of Pharmaceutical Interest," *Anal. Chem.*, 62, pp. 1714-1722, (1990). Month Not Available.

*Primary Examiner*—Louise Leary
*Attorney, Agent, or Firm*—Schwegman, Lundberg, Woessner & Kluth, P.A.

[57] ABSTRACT

Oligosaccharides are structurally characterized utilizing enzymatic digestion with an array of highly specific exoglycosidases followed by electrochemical detection and measurement of the molar quantity of cleaved monosaccharides in each enzymatic digest.

20 Claims, 4 Drawing Sheets

SEQUENCING OF OLIGOSACCHARIDES: THE REAGENT ARRAY-ELECTROCHEMICAL DETECTION METHOD

This invention was made with government support under grant BCS-9258652 (National Science Foundation). The Government has certain rights in this invention.

BACKGROUND OF THE INVENTION

Numerous research problems of modern biochemistry are associated with complex glycoproteins. The importance of various carbohydrate moieties, also known as sugar moieties, in glycoproteins is wide-ranging. They are known generally to be involved in protein targeting, cell-cell recognition, and antigen-antibody reaction (J. C. Paulson, *Trends Biochem. Sci.*, 14, 272 (1989)).

Major pharmaceutical companies and many startup biotechnology firms have initiated intense research efforts directed toward the discovery and production of carbohydrate-based drugs. The number of startup biotechnology companies capitalizing on new discoveries of carbohydrate-based drugs for cardiovascular, infectious, and autoimmune diseases is growing rapidly. Fueling these efforts has been the development and application of large scale mammalian cell culture for protein expression. Mammalian-cell-expressed recombinant glycoproteins that are approved or under development as pharmaceutical agents include, for example, tissue plasminogen activator, erythropoietin, soluble CD4, factor VIII, and β-interferon. The carbohydrate moieties of recombinant glycoproteins of pharmaceutical interest are known to influence protein activity, affect the solubility and stability of the protein, and possibly be involved in removal of the protein from circulation and targeting to a particular tissue (M. W. Spellman, *Anal. Chem.*, 62, 1714 (1990)). The need for simple and reliable methods of carbohydrate structural analysis is thus increasingly important (M. Geisow, *Bio/Technology*, 10, 277 (1992)). However, bioanalytical methodologies for carbohydrate structural analysis appear to be lagging behind similar capabilities that are being rapidly developed for proteins and genes.

Current techniques for carbohydrate structural characterization as commercialized by Oxford Glycosystems (C. T. Edge et al., *Proc. Nat'l. Acad. Sci., U.S.A.*, 89, 6338 (1992)) and Glyko (P. Jackson, *Biochem. J.*, 270, 705 (1990)) involve the collection of enzymatic digestions and the separation of remaining uncleaved oligosaccharides by gel permeation chromatography and gel electrophoresis, respectively. These techniques require prior labelling of oligosaccharides at the reducing terminus using a fluorescent or radioactive label.

One of the most commonly used approaches for carbohydrate sequencing is sequential digestion of an oligosaccharide with exoglycosidases of known and well-defined specificities (A. Kobata, in *Biology of Carbohydrates, Volume 2*, V. Ginsburg et al., ed., John Wiley & Sons, New York, pp. 88 ff. (1984); A. Kobata, *Anal. Biochem.*, 100, 1 (1979)). Typically, tritiated sodium borohydride ($NaB[^3H]_4$) is used to reduce and label an oligosaccharide of interest. The tritium-labelled sample is subjected to enzymatic digestion by bringing it into contact with an exoglycosidase. The presence of a particular monosaccharide unit at a non-reducing terminus, and perhaps also linkage information relative to that monosaccharide unit (e.g., linkage at a specified hydroxyl site on the ring, and/or in a specified α or β configuration), is detected by the ability of a given enzyme to cleave the disaccharide linkage connecting the terminal monosaccharide unit to the oligosaccharide chain.

The relative size of the labelled oligosaccharide fragment remaining in the reaction mixture after enzymatic digestion can be determined by measuring the hydrodynamic volume of the oligosaccharide fragment. Hydrodynamic volume is a parameter that reflects the flow speed of a solvated molecule, such as an oligosaccharide, through a porous material. The elution time is related to size of the molecule. Paper chromatography, gel electrophoresis, and gel permeation chromatography are typically used to measure hydrodynamic volume. A cleavage event causes a reduction in molecule size by reducing chain length. Cleavage can thus be detected indirectly by comparing the hydrodynamic volume of the remaining oligosaccharide fragment to the hydrodynamic volume observed for the uncleaved oligosaccharide. Because the tritium label in a tritium-labelled sample is located at the reducing terminus of the carbohydrate chain, the digestion product recovered from paper chromatography can be used for the next enzyme digestion in the sequential digestion protocol. Gel electrophoresis or gel permeation chromatography are now more commonly used in place of paper chromatography.

A major disadvantage of sequential digestion is that it requires the repeated isolation and determination of the oligosaccharide hydrodynamic volume (e.g., by paper chromatography, gel permeation chromatography, or gel electrophoresis) before and after each enzyme incubation. In addition to the time and effort necessary to carry out these separations, a further disadvantage is that the amount of starting material must be large to accommodate the unavoidable separation losses that accompany the repeated separations, dilutions, and concentrations.

An enzyme array method (C. T. Edge et al., *Proc. Nat'l. Acad. Sci., U.S.A.*, 89, 6338 (1992); R. A. Dwek et al., U.S. Pat. No. 5,100,778, issued Mar. 31, 1992)), also known more broadly as a reagent array analysis method, was developed to reduce the number of measurements of hydrodynamic volume needed to sequence an oligosaccharide. In the enzyme array method, a sample of a labelled oligosaccharide is divided into a number of aliquots, and each aliquot is incubated with a precisely defined mixture of structurally specific exoglycosidases. The exoglycosidases cleave monosaccharides from the nonreducing terminus of the oligosaccharide until a glycosidic linkage is reached that cannot be cleaved by any of the exoglycosidases present in that mixture. The uncleaved oligosaccharide fragment remaining in an aliquot is thus identified by the inability of an enzyme mixture lacking a given enzyme to cleave that linkage (a stop point) and the ability of the other enzymes to cleave the linkages up to that point. The typical result is an enzymatic digest containing a mixture of cleaved monosaccharide units and an uncleaved oligosaccharide fragment. Each digest will contain a different uncleaved oligosaccharide fragment depending on the enzyme mixture it contains. These fragments are then analyzed for their hydrodynamic volumes by gel permeation chromatography (C. T. Edge et al., *Proc. Nat'l. Acad. Sci., U.S.A.*, 89, 6338 (1992)) or gel electrophoresis (P. Jackson, *Biochem. J.*, 270, 705 (1990)). Taken together, a knowledge of the specificity of the exoglycosidases in each mixture and the hydrodynamic volume of the uncleaved oligosaccharide fragments ideally allows an identification of the sequence of the original oligosaccharide.

The enzyme array method of carbohydrate sequencing, while representing a significant improvement over sequencing schemes based on. sequential digestions. is still a complicated and cumbersome procedure. Hydrodynamic volume of the uncleaved oligosaccharide fragment must still be determined, and the oligosaccharide must initially be labelled in order to subsequently detect the uncleaved fragment. What is needed is an enzyme-based carbohydrate sequencing method that can be carried out without the need to label the oligosaccharide or measure the hydrodynamic volume of the uncleaved oligosaccharide fragment.

SUMMARY OF THE INVENTION

The present invention provides a method for structurally characterizing oligosaccharides. An oligosaccharide is reacted with an array of reagents, preferably exoglycosidases, to produce cleaved products characterized by one or more monosaccharides and a remaining oligosaccharide fragment. The reagents used in the array contain at least one cleaving agent having a cleavage specificity for a disaccharide linkage present in the oligosaccharide. In a preferred embodiment, the reagents in the array contain one or more exoglycosidases. One reagent, the positive control, contains a mixture of all the exoglycosidases used. Each remaining reagent contains a mixture of all but one of the exoglycosidases, which excluded exoglycosidase is included in all the other remaining reagents. A negative control, containing none of the exoglycosidases, is also provided. The missing exoglycosidase in each reagent determines the "stop point" for the enzymatic cleavage of the oligosaccharide in a given reaction mixture. The "stop point" determines the identity of the remaining, uncleaved oligosaccharide fragment.

The molar quantity of the cleaved products is determined by contacting each reaction mixture with an electrode to elicit an electrochemical response, then comparing the electrochemical responses elicited from each reaction mixture. Preferably, the electrochemical responses are elicited using pulsed amperometric detection (PAD). The molar quantity of cleaved products, preferably the total molar quantity of monosaccharides, is correlated with the cleavage specificities of the cleaving agents in order to structurally characterize the oligosaccharide.

DETAILED DESCRIPTION OF THE INVENTION

Figure 1:
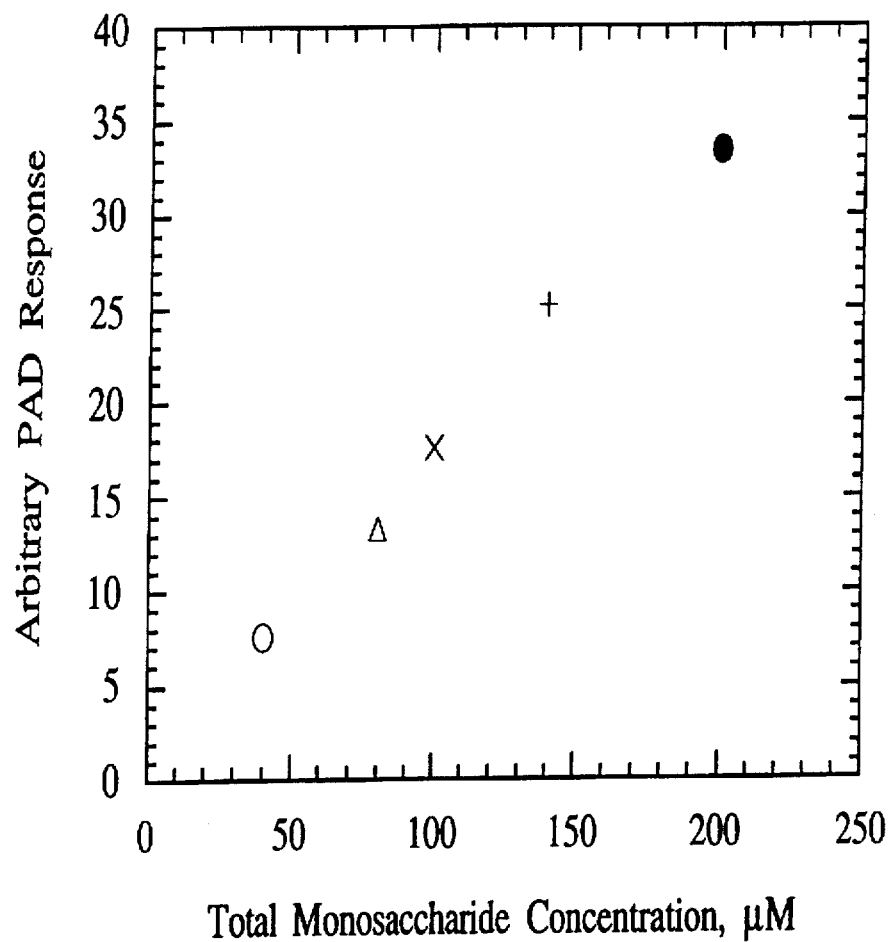
FIG. 1. Pulsed amperometric detection (PAD) response to total monosaccharide concentration.

The present invention provides a rapid and sensitive reagent array-electrochemical detection method for structurally characterizing oligosaccharides. The method uses an array of cleaving agents, preferably exoglycosidases, to cleave specified disaccharide linkages present in an oligosaccharide, followed by electrochemical detection and quantification of cleaved products, preferably released monosaccharide units, to obtain structural information about the oligosaccharide. Structural information includes information about any of the following attributes of the primary structure of an oligosaccharide: the monomeric (monosaccharide) composition of the oligosaccharide and the order in which the monosaccharide units are linked, including the presence of any branched (e.g., biantennary or triantennary) structures; the linkage positions of the glycosidic (disaccharide) bonds that join together the monosaccharide units to form the polymer; and the linkage configuration ($\alpha$ or $\beta$) at the anomeric carbon involved in a glycosidic bond. The anomeric carbon is that carbon which contains the reactive carbonyl of a monosaccharide that can be involved in intramolecular hemiacetal formation or intermolecular glycosidic bond formation. The method of the invention can be conveniently used to either partially or fully characterize an oligosaccharide structure. For ease of reference and in accordance with general usage in the field of carbohydrate research, the terms "sequence" or "sequencing" as used herein in connection with carbohydrates refer generally to structural characterization of oligosaccharides as described in this paragraph, unless otherwise specified.

The method of the invention has several practical advantages over current enzyme array based carbohydrate sequencing methods, including simplicity, speed, and the ability to use small amounts of starting material. A particular advantage of the invention is that carbohydrate sequencing is accomplished in situ without the need to separate the remaining oligosaccharide fragment from the released monosaccharide units. The remaining oligosaccharide fragment may contain two or more monosaccharide units, and thus includes disaccharides. Moreover, the sequencing can be performed without prior labelling of oligosaccharides and/or monosaccharides. Other known sequencing protocols (e.g., R. A. Dwek et al., U.S. Pat. No. 5,100,778, issued Mar. 31, 1992; A–H. Ali et al., U.S. Pat. No. 5,284,558, issued Feb. 8, 1994) require the incorporation a label, typically a fluorescent or radioactive label, at the reducing terminus prior to sequencing.

Oligosaccharides are polymeric carbohydrates composed of monosaccharide units linked together via glycosidic bonds. They occur naturally as covalent modifications to glycomolecules such as glycolipids and glycoproteins, as described in more detail below. Because each monosaccharide unit in an oligosaccharide has several reactive hydroxyl groups, oligosaccharides can exhibit complex branching motifs in addition to a simple linear configuration. Each oligosaccharide typically has one reducing terminus, also known as the free reducing terminus, and one or more non-reducing termini, depending on whether or not the oligosaccharide is branched. The reducing terminus is typically characterized by an aldehyde functional group at the $C_1$ carbon in the open ring form of the terminal monosaccharide unit. A nonreducing terminus is located at the opposite end or ends of the polymeric chain. Thus, an unbranched (linear) oligosaccharide chain contains one reducing terminus and one nonreducing terminus, whereas a branched oligosaccharide chain has one reducing terminus and two or more nonreducing termini. The presence of a free (i.e., underivatized) reducing terminus on the oligosaccharide to be sequenced is preferred, but not required by the invention. Thus, the reducing terminus associated with an oligosaccharide chain may be oxidized, labelled, or otherwise derivatized prior to sequencing if desired.

A glycosidic bond or linkage is the covalent linkage formed between a carbonyl group at a reducing terminus (typically at $C_1$) of a monosaccharide unit and a hydroxyl group on the ring of a second monosaccharide unit. Where two sugar monomers are thus joined in a glycosidic linkage, the linkage is termed a disaccharide bond. The terms "disaccharide linkage" or "disaccharide bond" are used herein to describe each successive glycosidic linkage in an oligosaccharide.

An oligosaccharide sequenced according to the method of the invention can be natural or synthetic, and may or may not be derivatized. Derivatization may occur naturally, e.g. via enzymatic phosphorylation, or can be accomplished synthetically. The oligosaccharide preferably contains about 5–30 monosaccharide units, but may contain about 2–100 or more monosaccharide units. Preferably, the oligosaccharide sample contains only one oligosaccharide, but the invention may be performed using an oligosaccharide sample containing a plurality of oligosaccharides as well. In the event the sample contains a plurality of oligosaccharides, a plurality of oligosaccharide fragments may remain after contact with one or more cleaving agents.

A natural oligosaccharide particularly well suited to sequencing using the method of the invention is one that is derived from a glycoconjugate such as a glycoprotein or glycolipid. Preferably the oligosaccharide is an N-linked or an O-linked oligosaccharide released from a glycoprotein, or a synthetic equivalent thereof. An N-linked oligosaccharide is typically covalently attached to a protein at an asparagine residue, and an O-linked oligosaccharide is typically covalently attached at serine, threonine or hydroxylysine. Release of an oligosaccharide from a glycoconjugate may be accomplished enzymatically or nonenzymatically. For example, N-glycosidic linkages of N-glycosylpeptides and N-glycosylproteins can be cleaved by hydrazine or trifluoroacetic acid. O-linked oligosaccharides can be cleaved from glycoconjugates using dilute alkali solution via a beta elimination mechanism. Alternatively, an appropriate endoglycosidase, such as glycopeptidase or endo-α-N-acetylgalactosaminidase, may be used. Glycoproteins can be purified using techniques known in the art.

N-linked oligosaccharides are typically branched and share some structural similarity. They are divided into three groups: high mannose, complex, and hybrid. All three groups share a common $Man_3GlcNAc_2$ core sequence. High mannose structures contain only mannose residues in the branches, while the branches of complex oligosaccharides contain GlcNAc, galactose and sialic acid (most often N-acetylneuraminic acid). Hybrid oligosaccharides have structural features common to both high mannose and complex oligosaccharides. In contrast, O-linked oligosaccharides exhibit much greater variability. The only common structural element in all known O-linked sugar chains is a GalNAc attached to the protein hydroxyl group. Five different core structures have been identified for O-linked oligosaccharides, as described in J. D. Paulson, *Trends in Biol. Sci.*, 14, 272–276 (1989), incorporated herein by reference. The main source of structural diversity for both N-linked and O-linked oligosaccharide chains comes from variation in the attachment of the terminal sugars (typically α-linked sialic acid, fucose, galactose, N-acetylgalactosamine or N-acetylglucosamine), attached either singly or in combination to one or more hydroxyl groups of the extension or core structures. Over 20 different terminal glycosylation sequences have been identified.

The sequencing method of the invention is useful for oligosaccharides of either known or unknown structure. In the case of a known or putative structure, as where synthetic oligosaccharides are obtained from a commercial supplier or isolated from a glycoprotein of known or suspected structure, the enzyme array can be designed to verify or confirm the putative sequence, as described in more detail below and in Examples I and II. In the case of an unknown structure, an enzyme array containing a representative set of exoglycosidases, as described in Example III, may be employed to identify the sequence of the carbohydrate. If the oligosaccharide of unknown structure is known to be an N-linked oligosaccharide, knowledge of the common core structure of N-linked oligosaccharides, as described above, can be used to design a suitable enzyme array.

In a preferred embodiment of the invention, a plurality of aliquots is prepared from a sample containing an oligosaccharide to be sequenced. The oligosaccharide is chemically or enzymatically digested by reacting the aliquots with an array of reagents to produce a set of reaction mixtures. Each "reagent" contains at least one cleaving agent having a cleavage specificity for a disaccharide linkage present in the oligosaccharide. The cleaving agent is provided in an amount, and for a time, effective to cleave the oligosaccharide and thereby produce a plurality of cleaved products. The term "array of reagents" is used to convey the underlying principle of the cleavage protocol utilized in the present invention and further described as "Reagent Array Analysis" in Rademacher et al., U.S. Pat. No. 5,100,778 (Mar. 31, 1992), incorporated herein by reference. Essentially, two or more suitable cleaving agents are selected, and an array of reagents is prepared such that each reagent lacks one of the selected cleaving agents. In a variation of the invention, one or more reagents can lack two of the selected cleaving agents. Each aliquot is then reacted with a different reagent to cleave the oligosaccharide and produce a plurality of cleaved products. The reaction is typically carried out for a predetermined amount of time, or to a predetermined end point, such that the reaction is carried to completion. It is to be understood that in practicing the invention, particularly when sequencing an oligosaccharide of unknown structure, the array will sometimes contain reagents composed of cleaving agents having a cleavage specificity for a disaccharide linkage that is not present in a particular oligosaccharide being sequenced. Inclusion of such chemical or enzymatic cleaving agents cannot systematically be avoided when sequencing an oligosaccharide of unknown structure, and negative information may be gained by their inclusion. However, as will be understood by one skilled in the art, the invention is most efficiently practiced when only those agents that will cleave a disaccharide linkage present in the oligosaccharide are included in the array.

The invention can also include a negative control aliquot prepared from the oligosaccharide sample in addition to the aliquots reacted with the array of reagents. As disclosed more fully below, an electrochemical response is elicited from the negative control aliquot in addition to the reaction mixtures, and the molar quantity of a cleaved product in a reaction mixture is determined from the electrochemical responses of the reaction mixtures and the negative control aliquot.

Exoglycosidases are the preferred cleaving agents. They are enzymes that cleave monosaccharides from the non-reducing terminus of an oligosaccharide hydrolytically at a disaccharide linkage according to their individual enzymatic specificities (Kobata, A., in *Biology of Carbohydrates*, Volume 2, V. Ginsburg et al., ed., John Wiley & Sons, New York, pp. 88 ff. (1984)). Exoglycosidases useful in the invention are those that have known and preferably well-defined cleavage specificities. Nonenzymatic cleaving agents that cleave monosaccharides from the non-reducing terminus of an oligosaccharide may also be used in the invention, provided that the monosaccharides released in the cleavage reaction retain their characteristic free reducing terminus.

The cleavage specificity of an exoglycosidase is defined in terms of its glycon specificity (the type of terminal monosaccharide unit it cleaves from an oligosaccharide chain, e.g., glucose, mannose, etc.), and its aglycon specificity (i.e., the type of monosaccharide unit or other functional group linked to the terminal monosaccharide unit, and the ring position of that linkage in cases where the aglycon is a monosaccharide unit). The glycon specificity of an exoglycosidase typically extends to the anomeric configuration of the glycosidic linkage ($\alpha$ or $\beta$) that it cleaves.

Representative lists of useful exoglycosidases are found in A. Kobata, *Anal. Biochem.*, 100, 1 (1979), R. Parekh et al., PCT Application No. WO 92/19768 (Nov. 12, 1992), T. W. Rademacher et al., U.S. Pat. No. 5,100,778 (Mar. 31, 1992), and R. J. Linhardt et al., U.S. Pat. 5,284,558 (Feb. 8, 1994), all of which are incorporated herein by reference. It is to be understood that these lists are illustrative only and in no way limit the selection of exoglycosidases used in the reagent array digestion according to the invention. Exoglycosidases are typically highly specific, having a glycon specificity directed to a specified terminal monosaccaride in a disaccharide linkage characterized by a specified ($\alpha$ or $\beta$) anomeric configuration. Some exoglycosidases, however, are less specific with respect to the monosaccharide moiety that they cleave. For example, certain $\beta$-N-acetylhexosaminidases do not distinguish the epimeric configurations (i.e., the different configurations about a particular carbon atom) of the C-4 hydroxyl group of $\beta$-N-acetylglucosamine and $\beta$-N-acetylgalactosamine, and will cleave both $\beta$-glycosyl and $\beta$-galactosyl linkages. Aglycon specificity is generally also high, but again, some exoglycosidases show lower specificity. For example, *Diplococcus pneumoniae* $\beta$-galactosidase cleaves Gal$\beta$1$\rightarrow$4GlcNAc but not Gal$\beta$1$\rightarrow$3GlcNAc and not Gal$\beta$1$\rightarrow$6GlcNAc. Common useful exoglycosidases include, but are not limited to, galactosidases, mannosidases, fucosidases, acetylhexosaminidases, neuraminidases, sialidases and xylosidases.

The exoglycosidases or other chemical cleaving agents used to digest the oligosaccharide according to the invention thus sequentially cleave monosaccharides from the oligosaccharide according to their individual specificities until a linkage is reached that cannot be cleaved by any of the cleaving agents present in the mixture (a stop point). When digestion is complete the reaction mixture typically contains both monomeric (monosaccharide) and oligomeric (oligosaccharide) carbohydrate fragments. If, however, the reaction mixture contains no cleaving agents having a specificity for the disaccharide linkage(s) characterizing the non-reducing terminus (or termini) of the original carbohydrate sample, then the oligosaccharide will remain intact after digestion. The inclusion of negative control aliquot containing the oligosaccharide but none of the cleaving agents in the array is especially advantageous in that it is designed to yield an oligosaccharide fragment equivalent to the original oligosaccharide. On the other hand, if a reaction mixture contains cleaving agents having a specificity for each of the disaccharide linkages present in the oligosaccharide, the oligosaccharide contains no stop points and only monosaccharides will remain in the reaction mixture following enzymatic digestion. This is known as a positive control.

Thus, in a particularly preferred embodiment of the invention, the sample aliquots are reacted with an array of reagents that includes a control reagent and a plurality of enzyme reagents. The total number of reagents is equal to the number of sample aliquots. The enzyme reagents each differ from one another and contain one or more exoglycosidases. The exoglycosidases included in a reagent array are chosen to create a pattern of stop points that allow the oligosaccharide to be sequenced. The exoglycosidases preferably each have a cleavage specificity for a disaccharide linkage present in the oligosaccharide. They are provided in an amount, and for a time, effective to cleave the disaccharide linkage and produce a plurality of cleaved products. One enzyme reagent (the positive control) contains a mixture of all the exoglycosidases. Preferably, the exoglycosidases are chosen such that the positive control completely cleaves the oligosaccharide, leaving only monosaccharide cleaved products. The remaining enzyme reagents preferably each contain a mixture of all the exoglycosidases excluding one, which excluded exoglycosidase is included in each of the other remaining enzyme reagents. That is, each enzyme reagent (other than the positive control) is distinct from the others and contains all but one of the chosen exoglycosidases. In an alternative embodiment, more than one exoglycosidase is excluded from one or more enzyme reagents. The control reagent is a negative control containing none of the exoglycosidases.

Each reaction mixture produced by reaction of a sample aliquot with an enzyme reagent contains a plurality of cleaved products. Preferably, the total number of aliquots, including the aliquots used for the positive and negative controls, is two more than the number of different disaccharide linkages to be cleaved, and each disaccharide linkage is cleaved by only one of the exoglycosidases. Alternatively, the number of aliquots is at least two more than the number of different disaccharide linkages to be cleaved, each disaccharide linkage is cleaved by at least one exoglycosidase, and one or more of the disaccharide linkages is cleaved by more than one of the exoglycosidases (causing a degeneracy that may complicate interpretation of sequencing results). In this case, the enzyme reagents must be sufficient in number to compensate for the degeneracy caused by disaccharide linkages that are cleaved by more than one of the exoglycosidase. Degeneracies may be unavoidable, and even desirable, when the chosen exoglycosidases have overlapping but not coextensive specificities.

More than one reagent array can be used sequentially in order to obtain additional information about the oligosaccharide structure. For example, greater specificity can be achieved by repeating or expanding the reagent array using exoglycosidases with higher sensitivity. It can be advantageous to use a series of reagent arrays for an oligosaccharide sample of unknown structure to provide experimental direction and thereby minimize the overall number of exoglycosidases needed to characterize the structure. For example, the exoglycosidic composition of successive enzyme arrays can be selected using the results obtained in preceding enzyme array digestions.

The reaction mixtures produced from reaction of the sample aliquots with the array of reagents are subjected to electrochemical detection and quantification according to the invention. Specifically, each reaction mixture, including any positive or negative controls, is contacted with an electrode to elicit an electrochemical response. The electrochemical responses of the reaction mixtures are quantified and compared among each other to determine the molar quantity of a cleaved product, if any, present in a reaction mixture, as described in more detail below. Preferably, the cleaved product is a monosaccharide that has been released from the non-reducing terminus of the oligosaccharide, which released monosaccharide is also known as a monomer, monosaccharide cleaved product, or a monosaccharide unit. In that case, the total molar quantity of the monosaccharide cleaved products in each reaction mixture is preferably determined.

The elicitation of electrochemical response, and subsequent quantification of cleaved products, in particular released monosaccharides, is preferably accomplished using pulsed amperometric detection (PAD) (W. R. LaCourse et al., Anal. Chem., 62, 589A (1990)). Aldehyde moieties in oligosaccharides and monosaccharides, which characterize the free reducing terminus, can be detected with high sensitivity by oxidation at gold (Au) electrodes in alkaline media and at platinum (Pt) electrodes under a broad range of pH conditions. Sensitivity of PAD at Au electrodes is maximized under conditions of high alkalinity, and pH greater than 12 is commonly recommended. The need for pH control in PAD at a Au electrode is achieved by the continuous addition of 0.1 N NaOH solution into a flow cell housing all the electrodes.

Ordinarily, the PAD signal observed for an oligosaccharide is a function of its chain length (number of monosaccharide units). This is because an electrochemical signal is produced by oxidation of the hydroxyl groups, and the number of hydroxyl groups on an oligosaccharide is directly related to its chain length. The aldehyde group of a reducing carbohydrate, however, is more easily oxidized. The present invention takes advantage of this feature to create a PAD response that reflects the molar quantity of aldehydes rather than the molar quantity of hydroxyl groups. The molar quantity of aldehydes is a good measure of the molar quantity of carbohydrates, because each carbohydrate molecule generally contains only one aldehyde. In contrast, the molar quantity of hydroxyl groups is more reflective of a measure of the total mass of carbohydrates rather than the molar quantity of carbohydrates, since carbohydrates are generally hydroxylated on the ring carbons that are not involved in polymeric chain formation.

The PAD signal produced by an enzymatic digest is enriched for the aldehyde response by a judicious choice of detection potential within PAD waveforms (W. R. LaCourse et al., Anal. Chem., 62, 589A (1990)) and by controlling the flow rate of the NaOH solution, preferably 0.1 N NaOH, used to bring the reaction mixtures and control portions in contact with the electrode. A faster flow rate reduces the time a sample component spends in contact with the electrode, favoring the aldehyde signal because the aldehyde is oxidized faster than the hydroxyl group. Furthermore, the effect of flow rate on PAD response is also a function of the diffusion coefficient of an analyte. The diffusion coefficient of an analyte decreases with increased molecular weight. Monosaccharides will be less affected by an increase in flow rate than oligosaccharides because their higher diffusion coefficients translate into greater contact with the electrode due to Brownian motion. Thus, an increase in NaOH flow rate brings the PAD signal of oligosaccharides closer to that observed for monosaccharides in two ways: it minimizes the mass-dependent component of the observed PAD signal (i.e., that portion contributed by oxidation of hydroxyl groups) and it reduces the intensity of the signal attributable to an oligosaccharide relative to a monosaccharide by disproportionately reducing the amount of time the oligosaccharide is in contact with the electrode at the higher flow rate, due to its lower diffusion coefficient. Preferably, the PAD signal produced by a remaining oligosaccharide fragment is less than twice the signal produced by a monosaccharide unit, so that the signal level of the oligosaccharide does not imply the existence of an additional monosaccharide unit. More preferably, the PAD signal produced by a remaining oligosaccharide fragment is about 100–150% of the signal produced by a monosaccharide, most preferably it is about 100–130%.

Sensitivity decreases with too fast a flow rate, however, because the aldehyde group is not in contact with the electrode long enough to be consistently oxidized and produce a strong signal. The invention thus makes use of an optimized flow rate, which is one that is fast enough to prevent most of the hydroxyl groups on a carbohydrate from oxidizing and producing an electrochemical signal, yet slow enough to permit consistent oxidation of the aldehyde group on the carbohydrate. Preferably, the NaOH flow rate within the PAD cell is about 0.5–3 ml/minute, more preferably about 0.8–2 ml/minute, most preferably about 1.0–1.6 ml/minute. The PAD response of an oligosaccharide in a mixture containing no exoglycosidases can be used as a background signal against which the other monosaccharide measurements in the enzyme array analysis can be compared. When the oligosaccharide PAD signal has been subtracted from the observed PAD signal for an enzymatic digest, the remaining PAD signal is attributable to the monosaccharides in solution. The total monosaccharide concentration in each aliquot can thus be directly and rapidly quantified by PA without any sample pretreatment or carbohydrate derivatization, because individual monosaccharides (e.g., glucose, galactose, etc.) typically show essentially identical molar concentration response in PAD (see FIG. 1 and Example I). Preferably, the carbohydrate sample analyzed according to the method of the invention has a concentration of about 0.1–100 μM, more preferably about 5–50 μM, most preferably about 5–15 μM. For an N-linked oligosaccharide sample, which typically contains from about 5 to 20 monosaccharide units, the released monosaccharide concentrations in an enzymatic digest of a 10 μM solution of oligosaccharide are in the range of 50 to 200 μM, and can be measured by PAD in a matter of seconds.

PAD was previously employed to simply detect the presence of monosaccharides and oligosaccharides after separation using high performance anion-exchange chromatography (e.g., J. R. Barr et al., Anal. Biochem., 192, 181–192 (1991); M. W. Spellman, Anal. Chem., 62, 1714 (1990)). Quantification was problematic because of the different molar response factors attributable to monosaccharides eluting at different salt concentrations provided by a typical elution gradient (R. R. Townsend et al., Anal. Biochem., 174, 459 (1988). And until now, PAD had not been used to quantify the total molar amount of monosaccharides in an unseparated mixture of oligosaccharides and monosaccharides, as is produced in an enzyme array digestion.

Once determined, the molar quantities of the cleaved products are correlated with the cleavage specificities of the cleaving agents, such as exoglycosidases, present in each reagent, in order to structurally characterize the oligosaccharide. The structural information so obtained for each reaction mixture can include the identification of the uncleaved linkage (the stop point) and its position in the oligosaccharide chain. The stop point for each cleavage reaction is associated with a glycosidic linkage that cannot be cleaved by the exoglycosidases present in that digest. The identity of that linkage is inferred from the specificity of the omitted exoglycosidase. The location of that linkage within the carbohydrate chain is determined by evaluating the monosaccharide concentration of that digest in view of the monosaccharide content of other digests in the array and the linkages inferred from their stop points, as described for specific experiments in the Examples. Taken in combination, the reaction mixtures can thereby provide a detailed characterization of the oligosaccharide with respect to its monosaccharide composition, sequence, branching structure, and linkage configurations. Reconstruction of the starting oligosaccharide can be carried out by direct interpretation of the analysis results or by comparison of the analysis with a computer generated data base, based on either theoretical or experimental data, or both.

It will be appreciated that there is no need to separate any remaining oligosaccharide fragment from the released monosaccharides present in an enzymatic digest when the method of the present invention is used. Neither identification of the released monosaccharides, nor determination of the length of, or identity of, the remaining oligosaccharide fragment, is necessary. There have been other sequencing methods using sequential enzymatic digestion that relied upon detection of released monosaccharides rather than a determination involving the remaining oligosaccharide fragment. However, these sequencing protocols relied on chromatographic separation of the released monosaccharides (either by gas or liquid chromatography) from the remaining oligosaccharide fragment and the use of standards to identify the monosaccharides (J. S. Sawardeker et al., Anal. Chem., 37, 1602 (1965); Y. C. Lee, Meth. Enzymol., 28, 63 (1973)); they were not in situ techniques as provided by the present invention. That is, in these conventional methods sequencing information cannot be obtained directly from the reaction mixture without additional preparative steps, such as desalting the enzymatic reaction mixture using ion exchange chromatography or organic solvent extraction, followed by chromatographic separation of oligosaccharides from monosaccharides.

The method of the invention thus represents an elegant approach to carbohydrate sequencing without the need for oligosaccharide labelling or the use of separation techniques, such as gel permeation chromatography or gel electrophoresis, to identify remaining uncleaved oligosaccharide fragments.

Advantages of the invention are illustrated by the following examples. However, the particular materials and amounts thereof recited in these examples, as well as other conditions and details, are to be interpreted to apply broadly in the art of carbohydrate structural analysis and should not be construed to unduly limit the invention.

Example I. Sequencing of a Complex N-linked Oligosaccharide

The complex N-linked oligosaccharide 1 was purchased from Oxford Glycosystems (Rosedale, N.Y.). The abbreviations used are galactose (Gal), N-acetylglucosamine (GlcNAc), and mannose (Man).

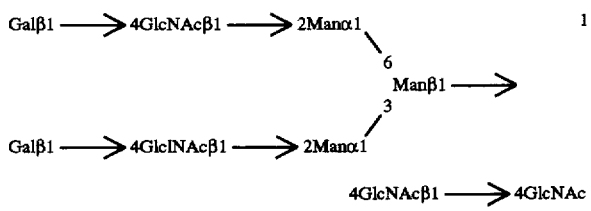

Exoglycosidases, including jack bean β-galactosidase, jack bean β-N-acetylhexosaminidase, diplococcus pneumoniae β-N-acetylhexosaminidase, jack bean α-mannosidase, achatina fulica β-mannosidase, bovine epididymal α-fucosidase, and almond meal α-¾-fucosidase were obtained from Sigma Chemical Company (St. Louis, Mo.) and Oxford Glycosystems (Rosedale, N.Y.). Monosaccharides were obtained from Sigma Chemical Company (St. Louis, Mo.). The specificities of these enzymes is set forth in A. Kobata, Anal. Biochem., 100, 1 (1979), incorporated herein by reference. The enzyme array used to analyze the oligosaccharide 1, designed on the basis of the known sequence of oligosaccharide 1 and containing various exoglycosidases at different concentrations, is set forth in Table I. Numbers refer to various enzyme mixtures (aliquots); the designation (○) refers to the absence of an enzyme, and (+) indicates the presence of an enzyme. Each enzyme unit is defined as the amount of enzyme that hydrolyzes one μmol of p-nitrophenyl glycoside per minute at 37° C. (A. Kobata, Anal. Biochem., 100, 1 (1979)).

TABLE I

Enzyme Array Used for Digestion of Oligosaccharide 1

| Exoglycosidase | Enzyme Mixture | | | | | | |
|---|---|---|---|---|---|---|---|
| | 1 | 2 | 3 | 4 | 5 | 6 | 7 |
| Jack bean β-galactosidase (8.2 unit) | ○ | ○ | + | + | + | + | + |
| Pneumoniae β-N-acetylhexosaminidase (0.25 unit) | ○ | + | ○ | + | + | + | + |
| Jack bean α-mannosidase (16.4 unit) | ○ | + | + | ○ | + | + | + |
| Achatina fulica β-mannosidase (1.6 unit) | ○ | + | + | + | ○ | + | + |
| Jack bean β-N-acetylhexosaminidase (8.2 unit) | ○ | + | ○ | + | + | ○ | + |

The enzyme mixtures were prepared in 0.1 M citric acid/0.2 M disodium phosphate/0.001% sodium azide (Sigma Chemical Company, St. Louis, Mo.) at pH 5.3 for the optimization of enzyme activities. The oligosaccharide 1 was divided into seven aliquots and digested with the exoglycosidase mixtures. Each aliquot was 100 μl and contained 15 μM of oligosaccharide 1. Enzymatic digestion of oligosaccharide was carried out at 37° C. for 24 hours and terminated by increasing solution pH to 12.

Pulsed amperometric detection (PAD) was performed at a gold (Au) electrode using a pulsed amperometric detector (Model PAD-2, Dionex Corporation, Sunnyvale, Calif.). Samples (1–50 μl volumes) were injected manually into the flow cell. A three-step waveform was used with detection at a constant potential (detection potential $E_{det}$=+0.05 V, detection time $t_{det}$=400 milliseconds (ms), integration time $t_{int}$=200 ms) followed by oxidative cleaning (oxidation potential $E_{oxd}$=+0.80 V, oxidation time $t_{oxd}$=360 ms) and reductive reactivation (reduction potential $E_{red}$=−0.60 V, reduction time $t_{oxd}$=540 ms) of the electrode. The response time was 3 seconds. Continuous addition of a 0.1 N NaOH solution was used to carrying oligosaccharides and monosaccharides over the electrode and keep the pH above 12. The flow rate was controlled by a HPLC pump (Hewlett Packard, Wilmington, De.).

The volume of the injection and the flow rate of NaOH carrying analytes over the Au electrode determine the detection limit and the dynamic range of monosaccharide concentration as measured by PAD. Using a 50 μl sample injection volume and 0.2 ml/minute NaOH flow rate, a detection limit of 1 μM monosaccharide (galactose) with a linear response time of more than three decades was established.

Subsequently, a calibration curve was prepared to evaluate the PAD response to total monosaccharide concentration in mixtures of monosaccharides. FIG. 1 shows a linear response of PAD to total monosaccharide concentration regardless of the monosaccharide composition of the mixture. The monosaccharide compositions evaluated were (○), 40 μM galactose; (Δ), a mixture of 40 μM galactose and 40 μM N-acetylglucosamine (80 μM total monosaccharide); (x), a mixture of 20 μM galactose, 20 μM N-acetylglucosamine, and 60 μM mannose (100 μM total monosaccharide); (+), a mixture of 40 μM galactose, 40 μM N-acetylglucosamine, and 60 μM mannose (140 μM total monosaccharide); and (●), a mixture of 40 μM galactose, 40 μM N-acetylglucosamine, 40 μM N-acetylgalactosamine, and 80 μM mannose (200 μM total monosaccharide). The detection limit for monosaccharides is in picomoles and the response is linear over more than three decades in concentration. It was concluded that these three monosaccharides commonly found in N-linked oligosaccharides (galactose, N-acetylglucosamine, and mannose) all exhibit similar molar response as measured by PAD.

Figure 2:
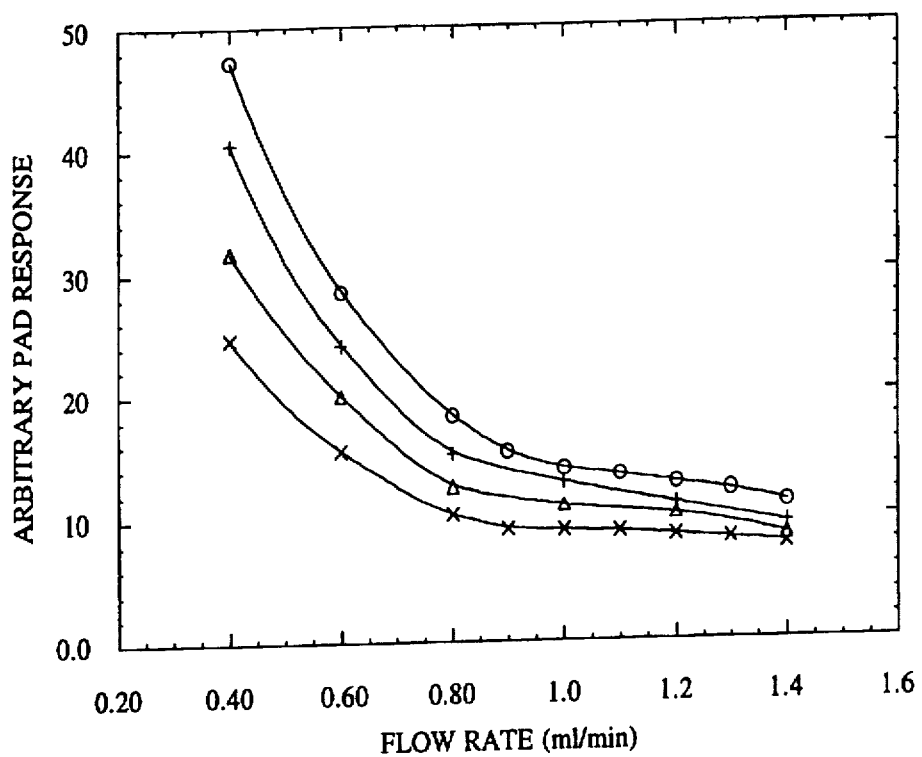
FIG. 2. Effect of NaOH flow rate on PAD response of monosaccharides and oligosaccharides.

Next, the PAD response for remaining uncleaved oligosaccharides was evaluated and standardized. FIG. 2 shows PAD responses to solutions containing (○) 15 μM oligosaccharide 1, (+) 15 μM Manβ1-4GlcNAcβ1-4GlcNAc, (Δ) 15 μM GlcNAcβ1-4GlcNAc and (x) 15 μM galactose as a function of NaOH flow rate over a range of 0.4 to 1.4 ml/minute. The observed ratio of PAD response of oligosaccharide 1 (○) to monosaccharide (galactose) (x) was 2.1 at the slowest flow rate of 0.4 ml/minute, decreasing to 1.3 at the fastest flow rate of 1.4 ml/minute. Because it is a multimeric polymer, oligosaccharide 1 has a smaller diffusion coefficient than the monosaccharide galactose. The PAD response to the oligosaccharide is thus expected to be more strongly affected by changes in the flow rate. As anticipated, the relative decrease in the PAD response of oligosaccharide as the flow rate was increased was greater than that observed for the monosaccharide.

At all flow rates studied, the PAD response of oligosaccharide 1 (symbolized by (○) in FIG. 2) was greater than that of the monosaccharide (symbolized by (x) in FIG. 2). Oligomeric constituents of oligosaccharide 1, namely the trisaccharide Manβ1-4GlcNAcβ1-4GlcNAc (symbolized by (+) in FIG. 2) and the disaccharide GlcNAcβ1-4GlcNAc (symbolized by (Δ) in FIG. 2) exhibited PAD responses intermediate between the responses observed for oligosaccharide 1 and the monosaccharide. Thus, the PAD responses of the remaining uncleaved oligosaccharides in an enzymatic digestion of oligosaccharide 1 were expected decrease as the enzymatic digestion progresses and those fragments become shorter. It was found, however, that at the flow rate of about 1.4 ml/minute the variation in the PAD response of oligomeric fragments during enzymatic digestion of oligosaccharide 1 could be confined within about 25% of the original signal exhibited by oligosaccharide 1 (see FIG. 2). With careful measurements at this flow rate, the background signal of an oligosaccharide was found to still be numerically distinguishable from the PAD signal attributable to monosaccharides, and integer molar quantities of monosaccharides could be calculated for each enzymatic digestion, as described below. For example, in FIG. 2, at a flow rate of 1.0 ml/minute, the arbitrary PAD signal of a monosaccharide is about 10, whereas the arbitrary PAD signal of an oligosaccharide is between about 12 and 15. Furthermore, the last enzyme mixture of a properly designed enzyme array contains all required exoglycosidases for the complete digestion of oligosaccharide. The number of total monosaccharides measured from complete digestion can be used as a final check for the interpretation of results in carbohydrate sequencing.

Figure 3:
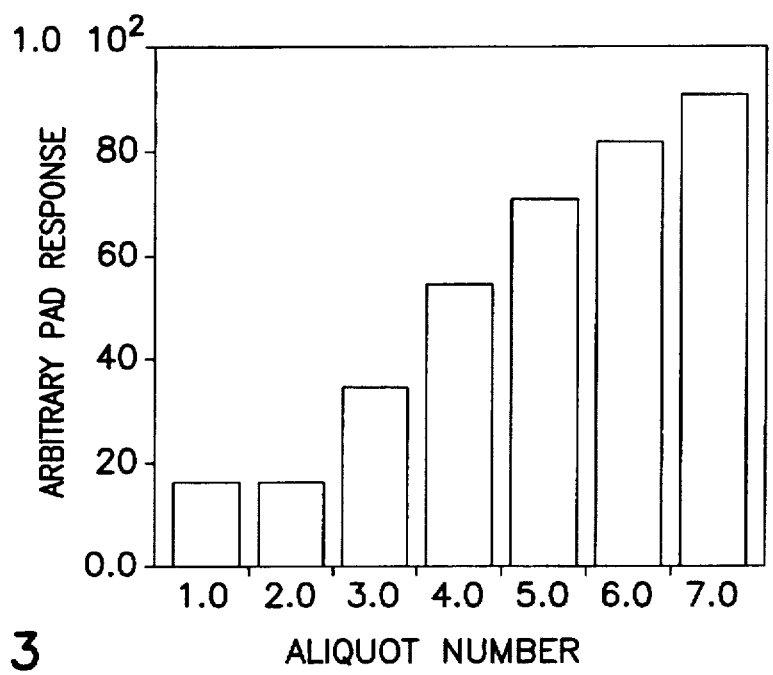
FIG. 3. Experimental PAD responses for digestion of 15 µM oligosaccharide 1 using the enzyme array set forth in Table I.

Based upon the above-described evaluation of the PAD response for oligosaccharides, a flow rate of 1.0 ml/minute was chosen to carry out a PAD analysis of the enzymatic digests of oligosaccharide 1 (15 μM) as specified in array shown in Table I. FIG. 3 reports the total PAD response observed for each enzymatic digest (20 μl sample injection volumes) in the array. By comparing these results to the expected monosaccharide and oligosaccharide PAD responses at the chosen flow rate (1.0 ml/minute) as shown in FIG. 2, the molar quantity (number) and the concentration of monosaccharides released in each digestion aliquot were quantitatively determined. These results are summarized in Table II.

TABLE II

Concentrations of Uncleaved Oligosaccharide 1 and Released Monosaccharide as Measured by PAD

| Aliquot Number | Oligosaccharide Concentration, μM | Released Monosaccharide | |
|---|---|---|---|
| | | Number | Concentration, μM |
| 1 | 15 | 0 | 0 |
| 2 | 15 | 0 | 0 |
| 3 | 15 | 2 | 30 |
| 4 | 15 | 4 | 60 |
| 5 | 15 | 6 | 90 |
| 6 | 15 | 7 | 105 |
| 7 | 0 | 9 | 135 |

None of the exoglycosidases was present in aliquot 1, thus the remaining uncleaved oligosaccharide is oligosaccharide 1 (see FIG. 3 for the PAD signals actually observed for each aliquot). This aliquot provided the background signal attributable to the remaining uncleaved oligosaccharide which was subtracted from the PAD responses for the other mixtures (see FIG. 3). Jack bean β-galactosidase was the only exoglycosidase missing from aliquot 2, but as it was needed to initiate cleavage from the nonreducing terminus, the remaining uncleaved oligosaccharide was still equivalent oligosaccharide 1. Both hexosaminidases were missing from aliquot 3, thus the stop point was the GlcNAcβ1→2Man linkage on each of the two branches, resulting two monomeric (galactose) cleaved products. Aliquot 4 was missing the α-mannosidase, thus the stop points were the two αmannose linkages to the mannose at the branch point, resulting in 4 monomeric cleaved products (2 galactose and 2 N-acetylglucosamine). The β-mannosidase was missing from aliquot 5, thus the stop point was the Manβ1→4GlcNAc linkage. Six monomeric cleaved products (2 galactose, 2 N-acetylglucosamine, and 2 mannose) were observed. Aliquot 6 was missing jack bean β-N-acetylhexosaminidase. Pneumoniae β-N-acetylhexosaminidase, which was present, cleaved the GlcNAcβ1→2Man linkage but not the GlcNAcβ1→4GlcNAc linkage. Thus, the remaining oligosaccharide fragment was GlcNAcβ1→4GlcNAc, and seven monomeric cleaved products (2 galactose, 3 N-acetylglucosamine, and 2 mannose) were observed. In aliquot 7, all the exoglycosidases were present, and the oligosaccharide was completely digested into nine monomeric cleaved products.

Thus, the measured monosaccharide numbers, in combination with the known specificities of the chosen exoglycosidases, provided a detailed characterization of oligosaccharide 1 in terms of its carbohydrate composition, linkage configuration (α or β), and glycosidic linkage position.

Example II. Sequencing of a Triply Branched Complex N-linked Oligosaccharide The complex N-linked oligosaccharide 2 was purchased from Oxford Glycosystems (Rosedale, N.Y.). The abbreviations used are galactose (Gal), N-acetylglucosamine, (GlcNAc), fucose (Fuc) and mannose (Man).

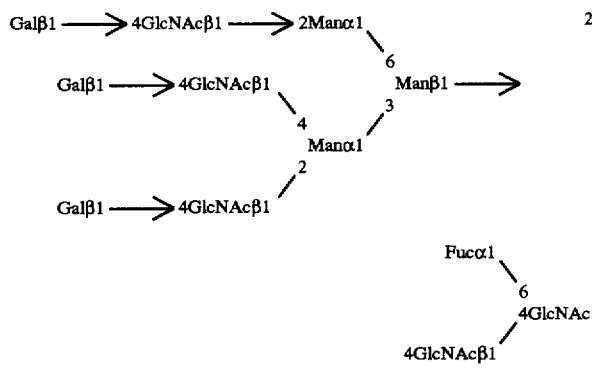

Exoglycosidases were purchased from Sigma Chemical Company (St. Louis, Mo.) and Oxford Glycosystems (Rosedale, N.Y.). The enzyme array used to analyze oligosaccharide 2 was designed on the basis of the known sequence of oligosaccharide 2 and is set forth in Table III. It contained a representative set of exoglycosidases (i.e., α- and β-mannosidases, β-N-acetylhexosaminidases, a β-galactosidase and an α-fucosidase) that are generally useful in analyzing N-linked oligosaccharides, which are made up primarily of mannose, N-acetylglucosamine, galactose, and fucose. Numbers refer to various enzyme mixtures (aliquots); the designation (o) refers to the absence of an enzyme, and (+) indicates the presence of an enzyme.

TABLE III

Enzyme Array Used for Digestion of Oligosaccharide 2

| Exoglycosidase | Enzyme Mixture | | | | | | | |
|---|---|---|---|---|---|---|---|---|
| | 1 | 2 | 3 | 4 | 5 | 6 | 7 | 8 |
| Jack bean β-galactosidase | o | o | + | + | + | + | + | + |
| Pneumoniae β-N-acetylhexosaminidase | o | + | o | + | + | + | + | + |
| Jack bean α-mannosidase | o | + | + | o | + | + | + | + |
| Achatina fulica β-mannosidase | o | + | + | + | o | + | + | + |
| Jack bean β-N-acetylhexosaminidase | o | + | o | + | + | o | + | + |
| Bovine epididymal α-fucosidase | o | + | + | + | + | + | o | + |

Figure 4:
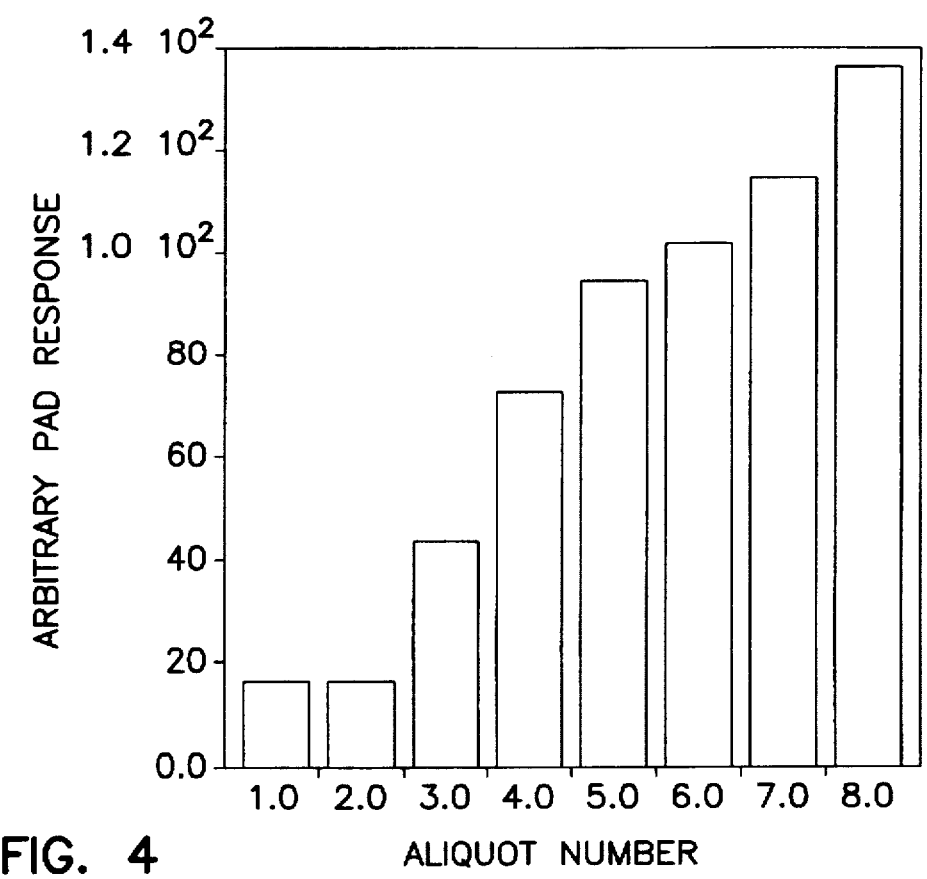
FIG. 4. Experimental PAD responses for digestion of 15 µM oligosaccharide 2 using the enzyme array set forth in Table III.

The enzyme mixtures were prepared, the enzymatic digestions were carried out, and pulsed amperometric detection of cleaved products was performed as set forth in Example I. FIG. 4 reports the total PAD response observed for each enzymatic digest (15 μM oligosaccharide 2, 20 μl sample injection volumes) in the array. By comparing these results to the expected monosaccharide and oligosaccharide PAD responses at the chosen flow rate (1.0 ml/minute) as shown in FIG. 2, the molar quantity (number) and the concentration of monosaccharides released in each digestion aliquot were quantitatively determined. These results are summarized in Table IV.

TABLE IV

Concentrations of Uncleaved Oligosaccharide 2 and Released Monosaccharide as Measured by PAD

| | Oligosaccharide | Released Monosaccharide | |
|---|---|---|---|
| Aliquot Number | Concentration, μM | Number | Concentration, μM |
| 1 | 15 | 0 | 0 |
| 2 | 15 | 0 | 0 |
| 3 | 15 | 3 | 45 |
| 4 | 15 | 6 | 90 |
| 5 | 15 | 8 | 120 |
| 6 | 15 | 9 | 135 |
| 7 | 15 | 10 | 150 |
| 8 | 0 | 12 | 180 |

None of the exoglycosidases was present in aliquot 1, thus the remaining uncleaved oligosaccharide was oligosaccharide 2. This aliquot provided the background signal attributable to the remaining uncleaved oligosaccharide which was subtracted from the PAD responses for the other mixtures. Jack bean β-galactosidase was the only exoglycosidase missing from aliquot 2, but as it was needed to initiate cleavage from the nonreducing terminus, the remaining uncleaved oligosaccharide was still equivalent oligosaccharide 2. Both hexosaminidases were missing from aliquot 3, thus the stop points were the GlcNAcβ1→4Man linkages on each of the three branches, resulting three monomeric (galactose) cleaved products. Aliquot 4 was missing the α-mannosidase, thus the stop points were the two αmannose linkages to the mannose at the first branch point, resulting in six monomeric cleaved products (3 galactose and 3 N-acetylglucosamine). The β-mannosidase was missing from aliquot 5, thus the stop point was the Manβ1→4GlcNAc linkage. Accordingly, eight monomeric cleaved products (3 galactose, 3 N-acetylglucosamine, and 2 mannose) were observed. Aliquot 6 was missing jack bean β-N-acetylhexosaminidase. Pneumoniae β-N-acetylhexosaminidase, which was present, cleaved the GlcNAcβ1→Man linkages but not the GlcNAcβ1→4GlcNAc linkage. Thus, nine monomeric cleaved products (3 galactose, 3 N-acetylglucosamine, and 3 mannose) were observed. Aliquot 7 was missing the fucosidase. All linkages except the Fuccα1→6GlcNAc linkage were cleaved by the enzymes present in the mixture, hence 10 monomeric cleaved products (3 galactose, 4 N-acetylglucosamine, and 3 mannose) were produced. In aliquot 8, all the exoglycosidases were present, and the oligosaccharide was completely digested into 12 monomeric cleaved products.

Example III. Sequencing of a High Mannose N-linked Oligosaccharide

The high mannose N-linked oligosaccharide 3 was purchased from Oxford Glycosystems (Rosedale, N.Y.). The abbreviations used are galactose (Gal), N-acetylglucosamine, (GlcNAc) and mannose (Man).

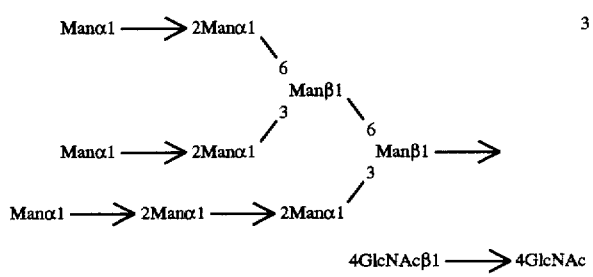

Exoglycosidases were purchased from Sigma Chemical Company (St. Louis, Mo.) and Oxford Glycosystems (Rosedale, N.Y.). The enzyme array used to analyze oligosaccharide 3 was the same as that used in Example II and is set forth in Table III. This array is not specifically designed with reference to the known sequence of oligosaccharide 3; instead it used to illustrate the sequencing of an N-linked oligosaccharide of unknown sequence. Numbers refer to various enzyme mixtures (aliquots); the designation (○) refers to the absence of an enzyme, and (+) indicates the presence of an enzyme.

Figure 5:
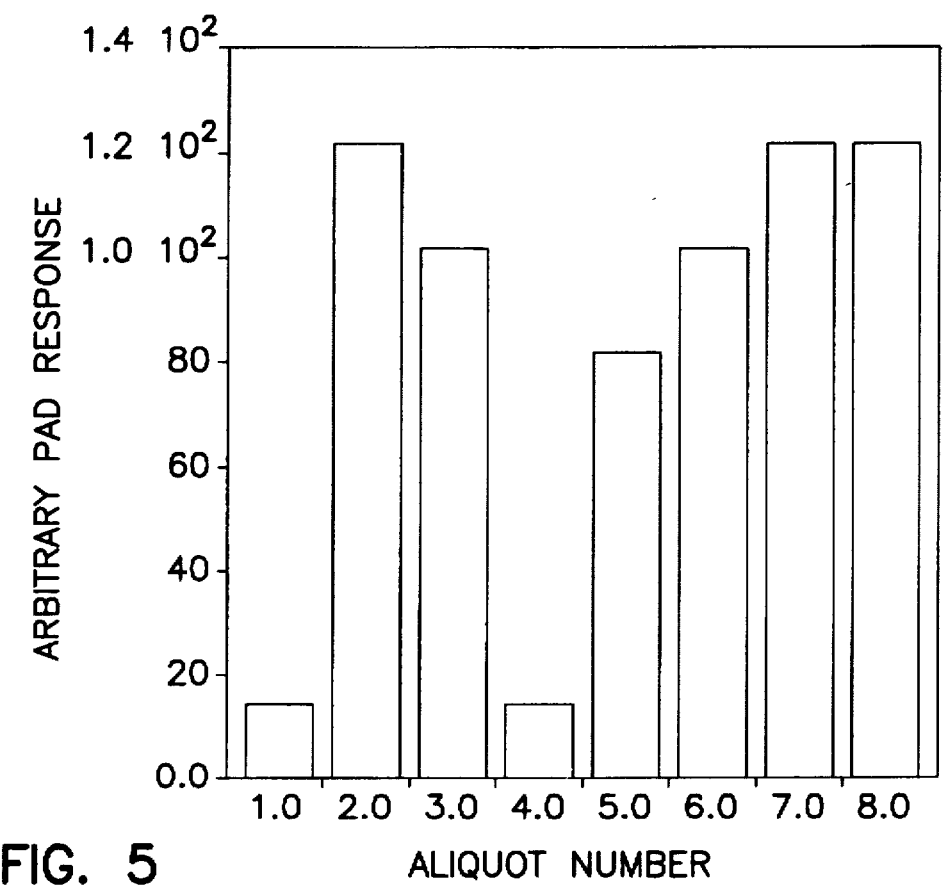
FIG. 5. Experimental PAD responses for digestion of 15 µM oligosaccharide 3 using the enzyme array set forth in Table III.

The enzyme mixtures were prepared, the enzymatic digestions were carried out, and pulsed amperometric detection of cleaved products was performed as set forth in Example I. FIG. 5 reports the total PAD response observed for each enzymatic digest (15 μM oligosaccharide 3, 20 μl sample injection volumes) in the array. By comparing these results to the expected monosaccharide and oligosaccharide PAD responses at the chosen flow rate (1.0 ml/minute) as shown in FIG. 2, the molar quantity (number) and the concentration of monosaccharides released in each digestion aliquot were quantitatively determined. These results are summarized in Table V.

TABLE V

Concentrations of Uncleaved Oligosaccharide 3 and Released Monosaccharide as Measured by PAD

| Aliquot Number | Oligosaccharide Concentration, μM | Released Monosaccharide Number | Concentration, μM |
| --- | --- | --- | --- |
| 1 | 15 | 0 | 0 |
| 2 | 0 | 11 | 165 |
| 3 | 15 | 9 | 135 |
| 4 | 15 | 0 | 0 |
| 5 | 15 | 7 | 105 |
| 6 | 15 | 9 | 135 |
| 7 | 0 | 11 | 165 |
| 8 | 0 | 11 | 165 |

The only enzymes in the array that were capable of cleaving at sites present in oligosaccharide 3 were jack bean α-mannosidase, achatina fulica β-mannosidase, and jack bean β-N-acetylhexosaminidase. Thus, in any mixture where all three of these exoglycosidases were present, complete digestion occurred and 11 monomeric cleaved products were observed. Aliquots 2, 7 and 8 each showed complete digestion (11 monomeric cleaved products). None of the exoglycosidases was present in aliquot 1, thus the remaining uncleaved oligosaccharide was oligosaccharide 3. This aliquot provided the background signal attributable to the remaining uncleaved oligosaccharide which was subtracted from the PAD responses for the other mixtures. Both hexosaminidases were missing from aliquot 3, thus the stop point of that mixture was the GlcNAcβ1→GlcNAc linkage, resulting in nine monomeric (all mannose) cleaved products. Aliquot 4 was missing the α-mannosidase, thus cleavage from the nonreducing termini was not initiated and the remaining oligosaccharide fragment was equivalent to oligosaccharide 3. The β-mannosidase was missing from aliquot 5, therefore the α-mannosidase present in the mixture cleaved until the two Manβ1 linkages were reached, resulting in seven monomeric cleaved products (all mannose). Aliquot 6 was missing jack bean β-N-acetylhexosaminidase, making the stop point the GlcNAcβ1→4GlcNAc linkage. There, nine monomeric cleaved products (3 galactose, 3 N-acetylglucosamine, and 3 mannose) were observed.

The foregoing detailed descriptions and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A method for structurally characterizing an oligosaccharide comprising:
   (a) reacting a plurality of aliquots prepared from an oligosaccharide sample with an array of reagents to produce a set of reaction mixtures, each reagent comprising at least one cleaving agent having a cleavage specificity for a disaccharide linkage present in the oligosaccharide, wherein each reagent is provided in an amount and for a time effective to produce a plurality of cleaved products;
   (b) contacting each reaction mixture with an electrode to elicit an electrochemical response;
   (c) determining the molar quantity of a cleaved product in a reaction mixture by comparing the electrochemical responses elicited from each reaction mixture; and
   (d) correlating the molar quantity of a cleaved product in a reaction mixture with the cleavage specificities of the cleaving agents in each reagent to structurally characterize the oligosaccharide.

2. The method of claim 1 wherein the oligosaccharide has a reducing terminus.

3. The method of claim 1 wherein the concentration of oligosaccharide in the sample is about 5–50 μM.

4. The method of claim 1 wherein the oligosaccharide is an N-linked oligosaccharide.

5. The method of claim 1 wherein the oligosaccharide contains about 5–20 monosaccharide units.

6. The method of claim 1 wherein at least one cleaving agent comprises an exoglycosidase.

7. The method of claim 6 wherein the exoglycosidase is selected from a group consisting of a galactosidase, a mannosidase, a fucosidase, a acetylhexosaminidase, a neuraminidase, a sialidase and a xylosidase.

8. The method of claim 1 wherein pulsed amperometric detection (PAD) is used to elicit the electrochemical response.

9. The method of claim 8 wherein pulsed amperometric detection is accomplished at a gold electrode at a pH greater than about 12.

10. The method of claim 9 wherein a flow of about 0.1 N NaOH is used to bring the reaction mixtures into contact with the electrode.

11. The method of claim 10 wherein the NaOH flow rate is about 0.5–3 ml/minute.

12. The method of claim 11 wherein the NaOH flow rate is about 1–1.6 ml/minute.

13. The method of claim 1 wherein the sample comprises a plurality of oligosaccharides.

14. The method of claim 1 wherein the total molar quantity of monosaccharide cleaved products in each reaction mixture is determined.

15. The method of claim 1 further comprising providing a negative control aliquot prepared from the oligosaccharide sample in addition to the aliquots reacted with the array of reagents, eliciting an electrochemical response from the negative control aliquot, and determining the molar quantity of a cleaved product in each reaction mixture from the electrochemical responses of the reaction mixtures and the negative control aliquot.

16. A method for structurally characterizing an oligosaccharide comprising:
   (a) reacting a plurality of aliquots prepared from an oligosaccharide sample with an array of reagents to produce a set of reaction mixtures, the array comprising a control reagent and a plurality of enzyme reagents, each enzyme reagent comprising one or more exoglycosidases each having a cleavage specificity for a disaccharide linkage present in the oligosaccharide, wherein each reagent is provided in an amount and for a time effective to produce a plurality of cleaved products, and wherein:
      (i) the reagents are equal in number to the number of aliquots,
      (ii) one enzyme reagent contains a mixture of all the exoglycosidases,
      (iii) the remaining enzyme reagents each contain a mixture of all the exoglycosidases excluding one exoglycosidase, which excluded exoglycosidase is included in each of the other remaining reagent units, and
      (iv) the control reagent contains none of the exoglycosidases;
   (b) contacting each reaction mixture with an electrode to elicit an electrochemical response;
   (c) determining the molar quantity of a cleaved product in a reaction mixture by comparing the electrochemical responses elicited from each reaction mixture; and
   (d) correlating the molar quantity of a cleaved product in a reaction mixture with the cleavage specificities of the exoglycosidases in each enzyme reagent to structurally characterize the oligosaccharide.

17. The method of claim 16 wherein:
   (a) the number of aliquots is two in number greater than the number of disaccharide linkages to be cleaved, and
   (b) each disaccharide linkage is cleaved by only one of the exoglycosidases.

18. The method of claim 16 wherein:
   (a) the number of aliquots is at least two in number greater than the number of disaccharide linkages to be cleaved;
   (b) each disaccharide linkage is cleaved by at least one of the exoglycosidases;
   (c) one or more of the disaccharide linkages is cleaved by more than one of the exoglycosidases; and
   (d) the enzyme reagents are sufficient in number to compensate for degeneracy caused by disaccharide linkages cleaved by more than one of the exoglycosidases.

19. The method of claim 16 wherein pulsed amperometric detection (PAD) is used to elicit the electrochemical response.

20. The method of claim 16 wherein the total molar quantity of monosaccharide cleaved products in each reaction mixture is determined.

* * * * *